United States Patent
Kanno

(10) Patent No.: US 8,181,654 B2
(45) Date of Patent: May 22, 2012

(54) CONDOM ROLLED ON A RIGID RING SHEATHED WITH A ROTOR

(76) Inventor: Yasushi Kanno, Kurukawa-gun (JP)

(*) Notice: Subject to any disclaimer, the term of this patent is extended or adjusted under 35 U.S.C. 154(b) by 396 days.

(21) Appl. No.: 10/573,771

(22) PCT Filed: Dec. 1, 2005

(86) PCT No.: PCT/JP2005/022592
§ 371 (c)(1),
(2), (4) Date: Sep. 24, 2008

(87) PCT Pub. No.: WO2007/010634
PCT Pub. Date: Jan. 25, 2007

(65) Prior Publication Data
US 2009/0007921 A1    Jan. 8, 2009

(51) Int. Cl.
*A61F 6/04* (2006.01)
*A61F 6/02* (2006.01)
*A61F 5/44* (2006.01)

(52) U.S. Cl. .......... 128/844; 128/842; 604/349

(58) Field of Classification Search ............ 128/844, 128/918, 842; 604/349
See application file for complete search history.

(56) References Cited

U.S. PATENT DOCUMENTS

| 4,817,593 A * | 4/1989 | Taller et al. ............ 128/844 |
| 5,163,448 A | 11/1992 | Foldesy |
| 5,853,006 A | 12/1998 | Metz |
| 2002/0139373 A1 * | 10/2002 | Griffiths ............ 128/844 |
| 2004/0089309 A1 * | 5/2004 | Tsugawa ............ 128/844 |
| 2004/0118408 A1 * | 6/2004 | Wang et al. ............ 128/844 |

FOREIGN PATENT DOCUMENTS

| JP | 60-102011 U | 7/1985 |
| JP | 3-9292 Y2 | 3/1991 |
| JP | 7-231905 A | 9/1995 |
| WO | WO 88/02624 A1 | 4/1988 |

* cited by examiner

*Primary Examiner* — Patricia Bianco
*Assistant Examiner* — Victoria J Hicks
(74) *Attorney, Agent, or Firm* — Leydig, Voit & Mayer, Ltd.

(57) ABSTRACT

A ring structure for rolling a tubular region of a condom. A condom held and rolled on a ring includes a rigid ring, a lubricant layer, and a rotor. As an opening in the tubular region of the condom is expanded, the rigid ring is sheathed via the lubricant layer with the rubber tube. The rubber tube rotates in the ring and the ring is removable after placement of the condom.

12 Claims, 4 Drawing Sheets

CONDOM ROLLED ON A RIGID RING SHEATHED WITH A ROTOR

TECHNICAL FIELD

The present invention relates to a ring structure on which the tubular region of a condom is rolled.

BACKGROUND ART

Use of condoms has been expanding, in increased recognition of its effectiveness for contraception and in preventing infection to sexually transmitted diseases. However, various products in various shapes were developed in the trend toward reduction in thickness, and there are efforts aimed at developing products that give more natural and pleasant impression of use and thus satisfying the demand of the people who want traditional functions as well as an additional function to improve sex life.

In the efforts above, there are various inventions aimed at tightening the neck region of the penis, preventing drop out of condom, elongating sexual act, and preventing leakage of semen (e.g., Japanese Unexamined Utility Model Publication No. 1994-36621, Japanese Unexamined Patent Publication No. 2002-136533, and Japanese Registered Utility Model No. 3055221). However, when part of condom is made narrower, the diameter of the condom when it is rolled up becomes narrower, causing a problem that it was difficult to ensure the diameter of the condom to a length sufficient for easy placement; and because of that, there was no commercially available condom product that sufficiently tightens of the penis.

There is an invention similar to the present invention of holding and rolling the condom as the opening thereof is expanded in the tubular region of the condom (International Application WO 88/02624), but the condom demanded time for removal of the placement aid and also caused a concern about the damage of the condom by friction between the placement aid and the condom during placement, because the rolled condom is fixed on the placement aid.

In addition, there is an invention aimed at tightening the neck of the penis with a ring for prevention of fall out of condom (e.g., Japanese Patent No. 2607222), which also demanded a labor to place a condom as well as a ring or the like.

As apparent from the fact that there are so many inventions and devices, reduction in the diameter of the tubular region of the condom and easiness in placement of condom give an incompatible problem.

SUMMARY OF THE INVENTION

An object of the present invention is to provide a condom that is easier in placement even when the tubular region of the condom is narrowed for tightening the neck region of the penis by expansion/shrinkage of condom, preventing drop out of condom, and elongating sexual act, and the object is achieved by the condom held and rolled on a rigid ring sheathed with a rotor (rigid ring sheathed, via a lubricant layer, with the rotor) as the opening in the tubular region of the condom is expanded, wherein the ring is removable after placement of the condom.

The "rigid ring sheathed with a rotor" according to the present invention will be described below. The rubber region at the proximal end of conventional condoms, which represents the core for rolling the condom on, is ring in shape. Although only the surface of the rubber ring seems to rotate, the condom is rolled thereon, while not only the surface but the entire rubber ring including its core is rotated. In the present invention, a ring structure containing an unrotatable core of a rigid material inside the conventional rubber ring that still retains the function to allow the condom to be rolled on by rotation is invented, and applied to the ring according to the invention.

The "rigid ring sheathed with a rotor" is defined as a rigid ring of which the surface is sheathed with the rotor rotatable around a member of the rigid ring.

For example, if a thread of beads connected at both ends forming a ring is called a bead ring, the "rigid ring sheathed with a rotor" is something like the bead ring, although the thread is replaced with a rigid ring. The rotor is a member having a function to rotate, like beads, around the member of the rigid ring as its rotation axis.

The term "rigid" in the rigid ring indicates that the ring has a rigidity withstanding the shrinkage force by condom even when the opening in the narrowed tubular region of condom is rolled on as it is expanded.

Even when the tubular region of the condom is narrowed, by holding the opening in the tubular region of the condom as it is expanded and rolling it on the rigid ring sheathed with the rotor, it becomes possible to place the condom, while rolling it on the penis in a similar manner to the traditional method; and thus, by the present invention, it is possible to obtain the advantages of making the condom narrower without any change in placement efficiency and also to overcome the problems of fall off of condom and elongate sexual act. In addition, the invention, which is applicable to any condom if it is tubular in shape, enables development of condom products that have the characteristics of conventional various kinds of commercial condoms and are reinforced in their effectiveness in prevention of leakage of semen, which is important for contraception, and allows improvement in contraceptive efficiency without changing the products familiar to the consumers.

DESCRIPTION OF THE PREFERRED EMBODIMENTS

An embodiment of the present invention will be described referring to drawings.

Figure 1:
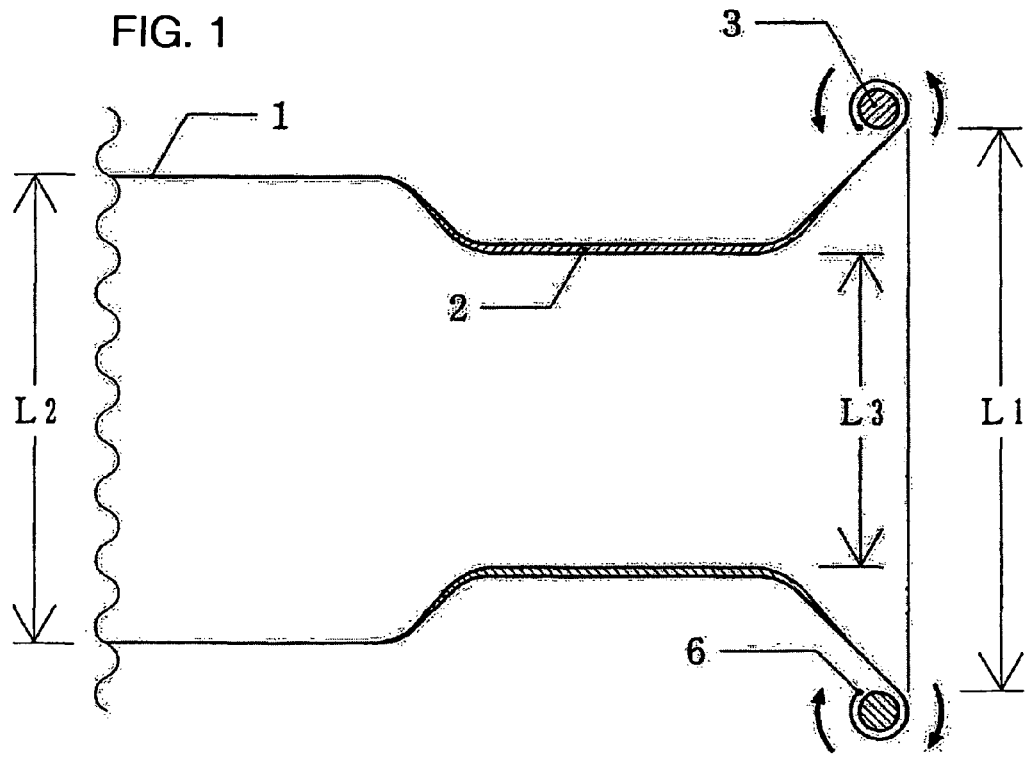
FIG. 1 is a sectional view illustrating the tubular region of a condom cut in a longitudinal direction.

FIG. 1 is a sectional view illustrating the tubular region of a condom (1) narrowed at its neck that is cut in a longitudinal direction.

(L1) represents an inner diameter of a rigid ring (3) sheathed with the rotor [hereinafter referred to as "ring (3)"]; (L2) represents a maximum diameter of the condom (1); and (L3) represents the inner diameter of the condom narrowed region (2).

Although the diameter (L3) of the condom is assumed to be smaller than the diameter (L2), the shape and position of the smaller-diameter region is not particularly limited, and the entire tubular region may be made narrower. Thus, the shape of the condom may be any one of commercially available products if it is tubular.

The diameter (L1) is set to be greater than the diameter (L2), and the ring (3) is used as a substitute for the conventional rolling rubber ring (6) for the condom (1).

The conventional rolling rubber (6) ring at the condom proximal end is made smaller than the ordinary size or eliminated, so that it may not interfere with the condom to be rolled on the ring (3).

The ring (3) is preferably an independent member, so that it can be removed after placement of the tubular region.

The ring (3) may be formed in a structure easily removable or may be adhered temporarily to the ring (3) when integrated with the tubular region; or the tubular region and one part of the ring (3) region may be formed as they are in the separable state.

Figure 2:
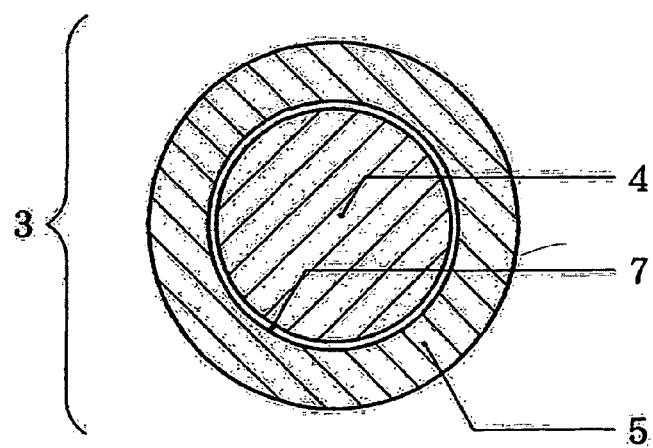
FIG. 2 is an expanded cross-sectional view illustrating a ring (3)

The configuration of the ring (3) will be described below, referring to FIG. 2. The ring (3) consists of a rigid ring (4), a rotor (5) rotating around a member of the rigid ring (4) and a lubricant layer (7).

Stainless steel may be used as the material for the rigid ring (4).

Stainless steel is higher in strength, resistant to rusting, and available at cheaper price. The rigid ring (4) may be made of any material if it does not deform when the condom is rolled on it, and thus, any one of other metals, plastics, hard rubbers, ceramics, and glass may be used.

A rubber tube made of a material as same as that used for condom may be used as the material for the rotor (5).

Because the rubber used for condom is superior in expansion and shrinkage, the rubber tube is expanded outside the ring and shrunk inside the ring, when the rubber tube is bent, attached to the rigid ring (4), and rotated around the lubricant layer of the ring. The rotation is more resistant when the rubber tube is less expandable and shrinkable, and thus, the rotor around the rigid ring (4) may be divided into pieces, like beads, when a rubber tube with less expandable and shrinkable is used.

When the rotor (5) is divided into pieces and a smooth through hole is formed in the rigid ring (4), like commercially available bead products, the friction thereof with the rigid ring (4) becomes smaller, making the rotation easier; and thus, it becomes possible to use harder materials such as metal, plastic, ceramic, and glass.

The lubricant layer (7) is formed on the area where the rigid ring (4) and the rotor (5) are in contact with each other, to make the rotor (5) rotatable around the rigid ring (4) more easily.

When the condom (1) is rolled on the ring (3) while expanded, the condom (1) applies a pressure from outside to inside of the ring (3) by shrinkage. The lubricant layer (7) is defined as a structure that allows smooth rotation of the rotor (5) during placement of the condom (1) even when such a pressure is applied to the ring (3). The rotatable structure may be formed, for example, by methods of using and not using the lubricant and the like or in combination thereof, but may be formed by any other method if the condom is easily rotatable.

Fluorine oil may be used as the lubricant for the lubricant layer (7).

The fluorine oil, which does not corrode rubbers and is superior in lubricity and durability, allow preservation of the properties of the rubber tube used for rotor (5) made of a material the same as that for the condom rubber for an extended period of time. Alternatively, a method of using a condom lubricant that does not affect the properties of rubbers may be used.

The lubricant layer (7) is only required to have a lubricant action, and thus, any other lubricant, oil, surfactant, jelly, or the mixture thereof may be used instead. The lubricant is preferably made of a component assuring long-term lubricity and not affecting various resistances such as water resistance, oil resistance, and chemical resistance of the materials for the rigid ring (4) and the rotor (5).

The method of using no lubricant may be a Teflon-processing method of forming a dry lubricant film for reducing the friction on the contact surface during rotation or a method of dividing the rotor (5) into bead-shaped pieces. Alternatively, a bead-shaped rotor may be used as the substitute for the lubricant layer (7) and covered with a rubber tube, which functions as a substitute for the rotor (5).

When a lubricant is used in the ring (3), the lubricant often causes leakage because of the pressure applied on the rotor (5) by the condom. It is preferable to make the end faces of the rubber tube adhere to each other and make a hollow O-ring for prevention of the leakage of lubricant. It is possible to prevent adhesion between the rigid ring (4) and the rubber tube because of the adhesive spilling out of the end faces of the rubber tube during the adhesion, by coating the adhesion region on the surface of the rigid ring (4) with a fluoroplastic resin.

Figure 10:
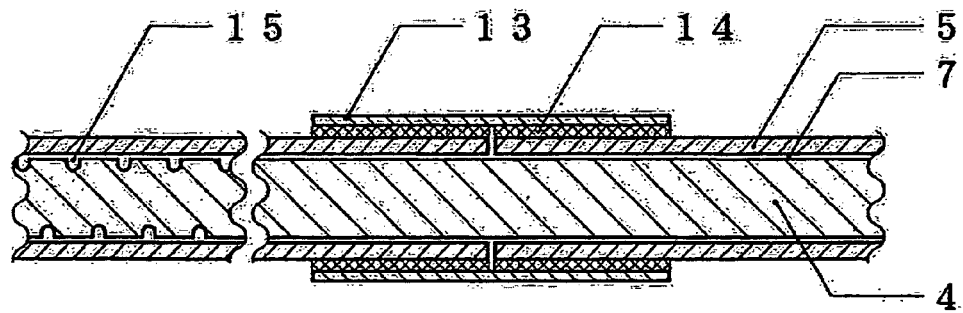
FIG. 10 is an expanded cross-sectional view illustrating the connection area of the rotor (5) rubber tube cut in the longitudinal direction

Alternatively, as shown in FIG. 10, a rubber tube (13) slightly larger in size may be placed and adhered (14) onto the connection area of the rubber tube, or an adhesive tape may be wound around it. Yet alternatively, it is also possible to use a method of performing a hairline processing or surface-roughening processing (15) for improvement in retention of the lubricant, for example, by laser irradiation or photoetching on the surface of the rigid ring (4), or a method of using these methods in combination.

Figure 3:
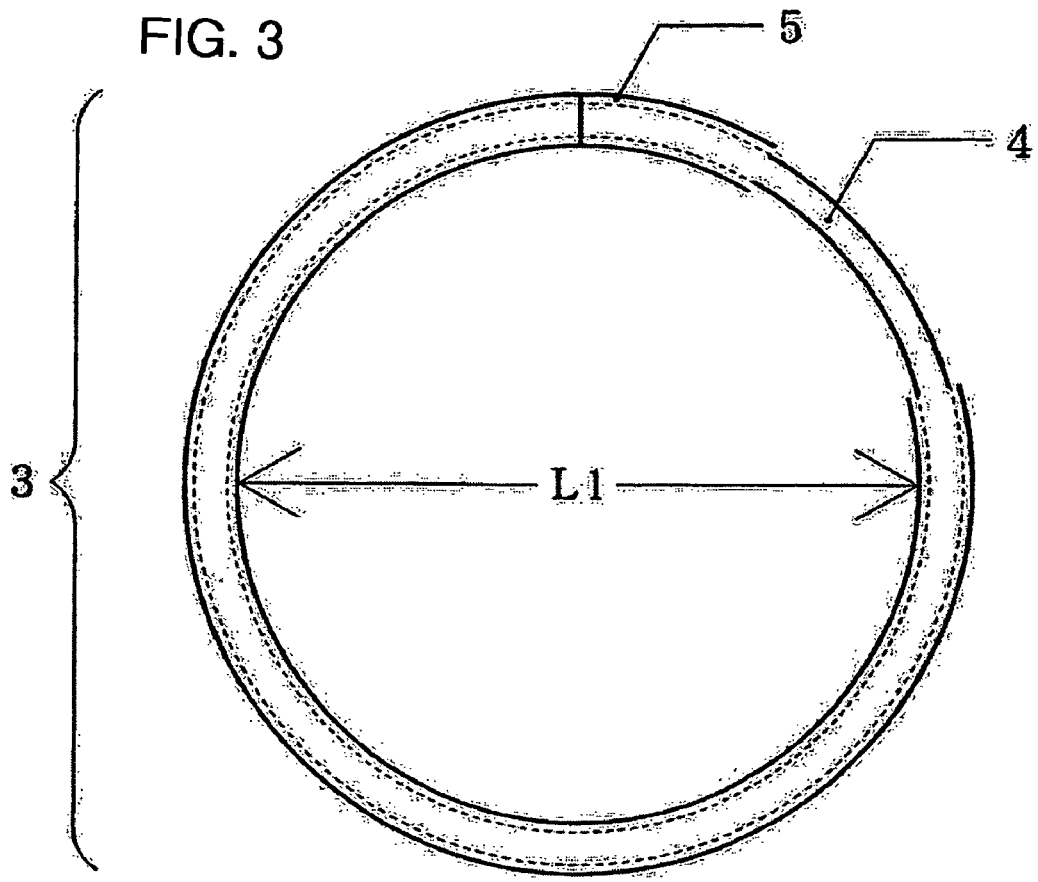
FIG. 3 is a top view illustrating the ring (3) (when a flexible rubber tube is used as a rotor (5))

FIG. 3 is a top view illustrating of the ring (3) having the rotor (5) of flexible rubber tube in the shape of hollow O-ring that is formed by adhering the end surfaces of the rubber tube to each other. Alternatively, the surface of the rigid ring (4) may be sheathed with a condom-like thin film in the hollow O-ring shape.

The shape of the ring (3) is not particularly limited if it is circular, and (L1) represents the inner diameter of the narrowest region of the ring (3) (e.g., minor axis when the ring is elliptical).

Figure 4:
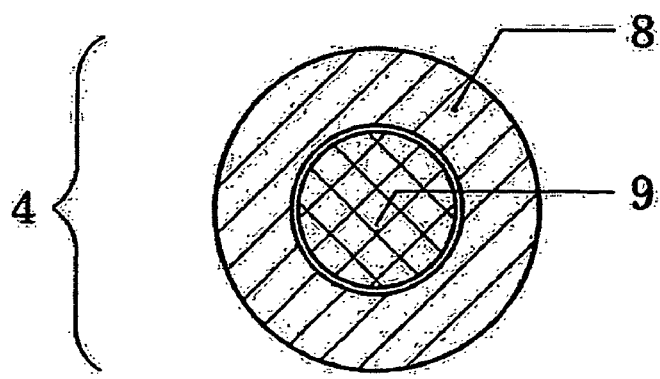
FIG. 4 is an expanded cross-sectional view illustrating a rigid ring (4)

FIG. 4 is an expanded cross-sectional view illustrating the rigid ring (4). In FIGS. 4 to 9, shown are the rigid rings (4) having the rigid tubes (8) and rigid wires (9) that are connected to each other, but the entire rigid rings (4) may be made of a single material, if these parts can be connected.

Figure 5:
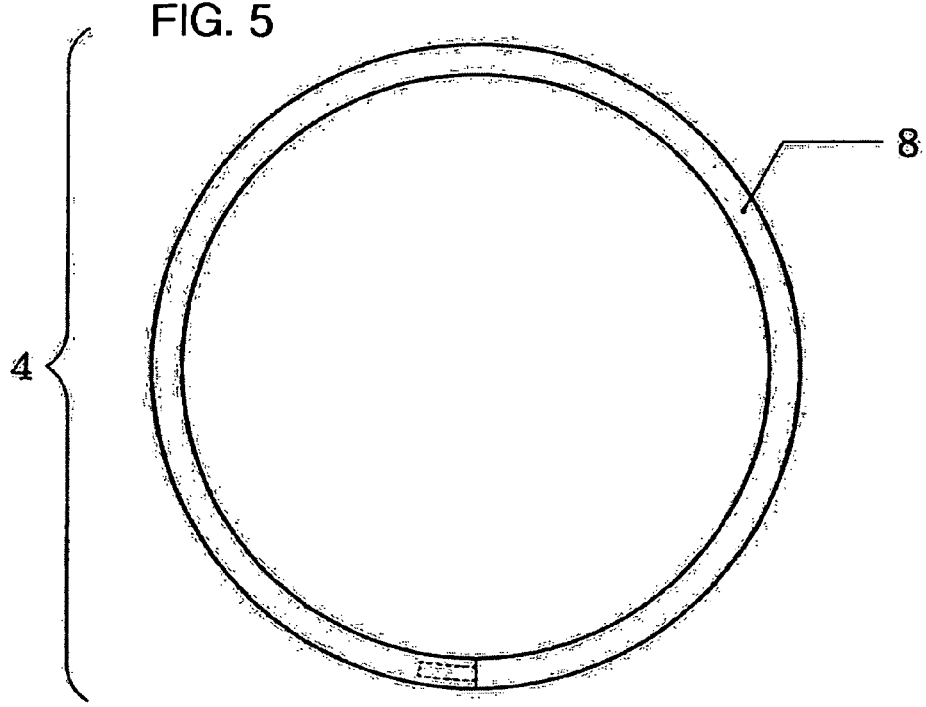
FIG. 5 is the top view illustrating the rigid ring (4)
Figure 6:
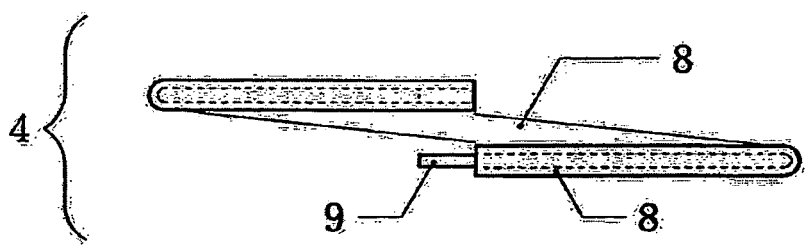
FIG. 6 is a side view illustrating the rigid ring (4) (spiral before ring connection)
Figure 7:
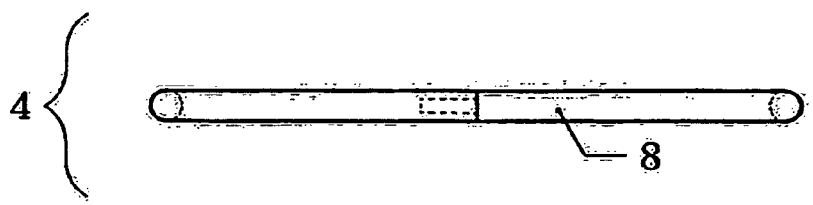
FIG. 7 is a side view illustrating the rigid ring (4) (after ring connection)

FIG. 5 is a top view of the rigid ring (4), and FIGS. 6 and 7 are side views of the rigid ring (4). FIG. 6 shows the rigid ring (4) formed in the spiral shape before the rotor (5) is placed, and FIG. 7 shows that when the rigid ring (4) is connected after the rotor (5) is placed, although the rotor (5) is not shown in the Figures.

Figure 8:
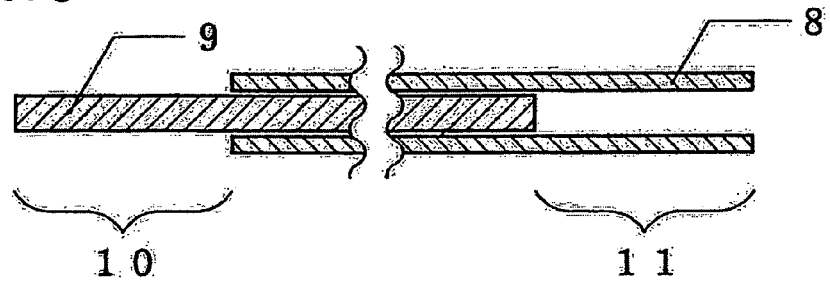
FIG. 8 is an expanded cross-sectional view illustrating the rigid ring (4) cut in the longitudinal direction (before ring connection)
Figure 9:
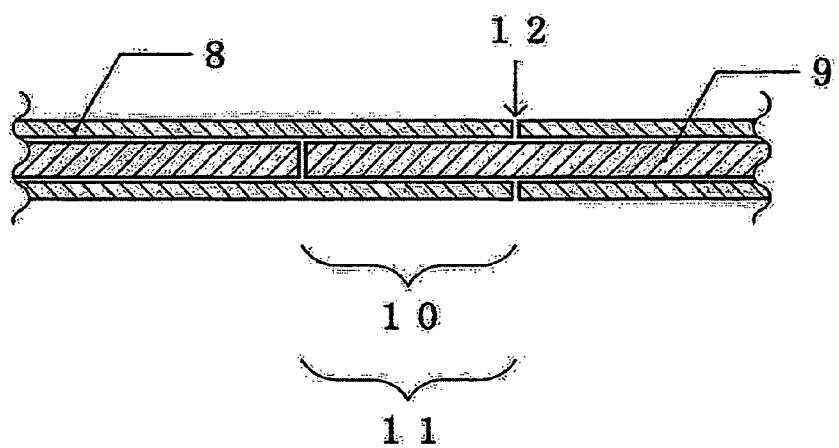
FIG. 9 is the expanded cross-sectional view illustrating the rigid ring (4) cut in the longitudinal direction (after ring connection)

FIGS. 8 and 9 are expanded cross-sectional views illustrating the ring connection area of the member of the rigid ring (4) cut in the longitudinal direction and show the procedure of processing into a ring.

As shown in FIG. 8, the rigid wire (9) is first inserted into the rigid tube (8), and as shown in FIG. 6, the composite is then bent into the C shape (spiral), giving a prototype of the rigid ring (4). The rigid ring (4) is then sheathed with a rotor (5).

Because the rotor (5) shown in FIG. 3 is an elastic rubber tube, the male region (10) and the female region (11) of the ring are connected to each other, while the rotor (5) is pressed in the longitudinal direction of the member of the rigid ring (4), both ends of the rigid ring (4) are held expanded toward outside, and the rigid ring (4) is brought into contact by its restoring force as shown in FIG. 9.

Because a contraction force of the condom (1) is applied onto the rigid ring (4), making the ring connection faces (12) push each other, the rigid ring is not needed to be adhered during connection if it does not separate sideways.

In another application, the ring (3) according to the present invention may be used for reduction in the period for surgeons to prepare emergency operation, while it is used for rolling the tubular region of long surgical gloves for the arms thereon, because such a ring allows easier placement of expandable and shrinkable articles as they are expanded in the tubular region.

INDUSTRIAL APPLICABILITY

The embodiments of the present invention are different from common condoms in that the condom is provided as product as it is expanded. Thus for commercialization thereof, it would be important to prevent deterioration of the condom by expansion. The restoring force of rubbery polymeric materials gradually deteriorate by mechanical fatigue when they are left expanded, and thus, these materials have a shortened use period, although it depends on the degree of expansion.

However, it is obvious from the fact that various products in various shapes have been developed in the trend toward reduction in thickness as described in the "BACKGROUND ART" that the consumers select their products not by the length of the use period but by the characteristics, function, and performance thereof.

Condoms are the necessary and consumable goods like foods for the consumers. Currently when the Internet purchasing and various delivery means are well advanced, a use period of as long as five years is not demanded any more, and the consumers purchase a planned quantity of condom products having a shorter use period, even if it is for example one year, according to its use period. Therefore, products having characteristics not found in other products and showing the effective period of the characteristics distinctively can meet the demand from a wide variety of consumers.

Products having a shorter expiration period is like foods having a limited freshness date, and it is possible to perform planned production and sales for shipment of the products in the world according to consumer demand, by constructing a system for connecting production line to distribution system of condoms, for example, like a reservation system for seat reservation in travel agencies.

In addition, there are some patented inventions that are useful in preventing deterioration by expansion, such as methods effective in restoring the shelf life and properties of rubber medical devices that are left in the expanded state (See Japanese Patent No. 3280182). It is a patent providing a packaging method that allows preservation of rubber products for an extended period of time without deterioration thereof and in the properties thereof, and that can elongate the storage stability thereof 4 to 8 times longer and preserve the properties thereof for one year or more when the rubber product is left expanded at an elongation of 20% or more of its breaking elongation, which was hitherto impossible.

With the measures to overcome the possible hurdle of the deterioration by elongation, the present invention has industrial applicability.

What is claimed is:

1. A condom assembly comprising:
   a condom having a tubular region with an opening and having an inside diameter; and
   a ring on which the tubular region of the condom is rolled, with the opening of the tubular region of the condom expanded by the ring, wherein the ring comprises:
      a rigid ring that is the core of the ring, wherein
         the rigid ring has an outside diameter larger than the inside diameter of the tubular region of the condom, and
         the rigid ring is sufficiently rigid to withstand compression by the condom without deformation;
      a rotor that is an annular hollow sheath covering the rigid ring, wherein
         the rotor and the rigid ring have a common circular central axis lying within the rigid ring,
         the rotor is rotatable about the common circular central axis with respect to the rigid ring, and
         the rigid ring is separated from the condom by the rotor; and
      a lubricant located within the rotor, between the rigid ring and the rotor, the ring being removable from the condom after unrolling of the condom from the ring by rotation of the rotor with resect to the rigid ring about the common circular central axis.

2. The condom assembly according to claim 1, wherein the rotor is a flexible rubber tube entirely covering the rigid ring.

3. The condom assembly according to claim 2, wherein, when the flexible rubber tube is rotated around the common circular central axis with respect to the rigid ring, the flexible rubber tube expands at the outside the ring and is compressed at the inside of the ring.

4. The condom assembly according to claim 1, wherein
   the tubular region of the condom includes at least two tubular regions having respective different inside diameters, and
   the tubular region of the condom is rolled onto and off of the ring by rotation of the rotor with respect to the rigid ring with respect to the rigid ring about the common circular central axis.

5. The condom assembly according to claim 1, wherein the ring is removably attached at the opening of the tubular region of the condom.

6. The condom assembly according to claim 1, wherein the rigid ring is a material selected from the group consisting of metals, plastics, hard rubber, ceramics, and glass.

7. A ring on which a condom having a tubular region with an opening and an inside diameter may be rolled, the ring comprising:
   a rigid ring that is the core of the ring, wherein
      the rigid ring has an outside diameter larger than the inside diameter of the tubular region of the condom, and
      the rigid ring is sufficiently rigid to withstand compression by the condom without deformation;

a rotor that is an annular hollow sheath covering the rigid ring, wherein
the rotor and the rigid ring have a common circular central axis lying within the rigid ring,
the rotor is rotatable about the common circular central axis with respect to the rigid ring, and
the rigid ring is separated from the condom by the rotor; and
a lubricant located within the rotor, between the rigid ring and the rotor, the ring being removable from the condom after unrolling of the condom from the ring by rotation of the rotor with respect to the rigid ring about the common circular central axis.

8. The ring according to claim 7, wherein the rotor is a flexible rubber tube entirely covering the rigid ring.

9. The ring according to claim 8, wherein, when the flexible rubber tube is rotated around the common circular central axis with respect to the rigid ring, the flexible rubber tube expands at the outside the ring and is compressed at the inside of the ring.

10. The ring according to claim 7, wherein the rigid ring of a material selected from the group consisting of metals, plastics, hard rubber, ceramics, and glass.

11. A condom assembly comprising:
a condom having a tubular region with an opening and having an inside diameter; and
a ring on which the tubular region of the condom is rolled, with the opening of the tubular region of the condom expanded by the ring, wherein the ring comprises:
a rigid ring that is the core of the ring, wherein
the rigid ring has an outside diameter larger than the inside diameter of the tubular region of the condom, and
the rigid ring is sufficiently rigid to withstand compression by the condom without deformation;
a flexible rubber tube that is an annular hollow sheath covering the rigid ring, wherein
the flexible rubber tube and the rigid ring have a common circular central axis lying within the rigid ring,
the flexible rubber tube is rotatable about the common circular central axis with respect to the rigid ring, and
the rigid ring is separated from the condom by the flexible rubber tube; and
a lubricant located within the flexible rubber tube, between the rigid ring and the flexible rubber tube, the ring being removable from the condom after unrolling of the condom from the ring by rotation of the flexible rubber tube with respect to the rigid ring about the common circular central axis.

12. The condom assembly according to claim 11, wherein, when the flexible rubber tube is rotated around the common circular central axis with respect to the rigid ring, the flexible rubber tube expands at the outside the ring and is compressed at the inside of the ring.

* * * * *

UNITED STATES PATENT AND TRADEMARK OFFICE
CERTIFICATE OF CORRECTION

PATENT NO. : 8,181,654 B2
APPLICATION NO. : 10/573771
DATED : May 22, 2012
INVENTOR(S) : Yasushi Kanno It is certified that error appears in the above-identified patent and that said Letters Patent is hereby corrected as shown below:

Title page, item (76) Inventor: Change "Kurukawa-gun (JP)" to --Miyagi (JP)--

Signed and Sealed this
Twelfth Day of March, 2013

Teresa Stanek Rea
*Acting Director of the United States Patent and Trademark Office*